United States Patent
Håkansson

(10) Patent No.: US 9,579,765 B2
(45) Date of Patent: Feb. 28, 2017

(54) CLEANING AND GRINDING OF SULFITE SENSOR HEAD

(71) Applicant: ALSTOM Technology Ltd, Baden (CH)

(72) Inventor: Rikard Håkansson, Vaxjo (SE)

(73) Assignee: General Electric Technology GmbH, Baden (CH)

( * ) Notice: Subject to any disclaimer, the term of this patent is extended or adjusted under 35 U.S.C. 154(b) by 500 days.

(21) Appl. No.: 13/871,823

(22) Filed: Apr. 26, 2013

(65) Prior Publication Data

US 2014/0069175 A1 Mar. 13, 2014

Related U.S. Application Data

(60) Provisional application No. 61/700,459, filed on Sep. 13, 2012.

(51) Int. Cl.
| | | |
|---|---|---|
| *B24B 27/033* | (2006.01) | |
| *G01N 27/38* | (2006.01) | |
| *G01N 3/08* | (2006.01) | |
| *G01N 33/28* | (2006.01) | |
| *G01N 29/024* | (2006.01) | |

(52) U.S. Cl.
CPC ............ *B24B 27/033* (2013.01); *G01N 3/08* (2013.01); *G01N 27/38* (2013.01); *G01N 29/024* (2013.01); *G01N 33/2823* (2013.01)

(58) Field of Classification Search
CPC ...... B24B 27/033; G01N 27/28; G01N 27/38; G01N 3/08; G01N 33/2823; G01N 29/024

USPC ........................................................ 73/61.41
See application file for complete search history.

(56) References Cited

U.S. PATENT DOCUMENTS

| | | |
|---|---|---|
| 5,002,651 A | 3/1991 | Shaw et al. |
| 5,767,845 A | 6/1998 | Oashi et al. |
| 7,244,348 B2* | 7/2007 | Fernandez et al. ........... 205/701 |
| 2009/0153155 A1* | 6/2009 | Chambon ........... A47J 37/1266 324/698 |
| 2011/0125412 A1* | 5/2011 | Salzer ..................... C02F 1/008 702/22 |

(Continued)

FOREIGN PATENT DOCUMENTS

| | | |
|---|---|---|
| CA | 2 173 464 | 2/1996 |
| CN | 86103809 A | 4/1987 |

(Continued)

OTHER PUBLICATIONS

English Machine Translation of Suzuki et al., JP 2008-134258 A.*

(Continued)

*Primary Examiner* — Hezron E Williams
*Assistant Examiner* — David Z Huang
(74) *Attorney, Agent, or Firm* — GE Global Patent Operation; Rita D. Vacca

(57) ABSTRACT

A sensor for detection and measurement of a particular substance present in a liquid is disclosed. The sensor includes a non-circular or non-symmetrically fixed electrode for detection and measurement of a particular substance present in a liquid in which said sensor is submersed. The sensor with non-circular or non-symmetrically fixed electrode and method of using the same reduces or eliminates electrode deformation upon residue removal therefrom thereby prolonging operating life.

12 Claims, 6 Drawing Sheets

(56) References Cited

U.S. PATENT DOCUMENTS

2013/0037263 A1* 2/2013 Cheung .............. G01N 33/2823
166/250.01

FOREIGN PATENT DOCUMENTS

| | | |
|---|---|---|
| EP | 0 859 228 | 8/1998 |
| GB | 2 092 306 | 8/1982 |
| JP | 45-023996 | 9/1970 |
| JP | 52-140879 | 11/1977 |
| JP | 52-147090 | 11/1977 |
| JP | 52147089 U | 11/1977 |
| JP | 6048148 U | 4/1985 |
| JP | 0950437 A | 2/1997 |
| JP | 10288592 A | 10/1998 |
| JP | H10-288593 A | 10/1998 |
| JP | 2007114216 A | 5/2007 |
| JP | 2008134258 A * | 6/2008 |
| JP | 2008134258 A | 6/2008 |
| JP | 2009092456 A | 4/2009 |
| JP | 2009524045 A | 6/2009 |
| JP | 2011141168 A | 7/2011 |

OTHER PUBLICATIONS

Unofficial English translation of Office Action issued in connection with corresponding JP Application No. 2013-190564 on Aug. 11, 2014.

Unofficial English translation of Notice of Allowance issued in connection with corresponding JP Application No. 2013-190564 dated Feb. 8, 2016.

* cited by examiner

CLEANING AND GRINDING OF SULFITE SENSOR HEAD

CROSS-REFERENCE TO RELATED APPLICATION

This application claims the benefit of U.S. Provisional Patent Application Ser. No. 61/700,459; filed on Sep. 13, 2012, entitled "CLEANING AND GRINDING OF SULFITE SENSOR HEAD" which is incorporated herein by reference in its entirety.

FIELD OF THE INVENTION

The present invention relates to a method and an apparatus for cleaning and grinding sulfite sensor heads, and more specifically, to a method and an apparatus for cleaning and grinding sulfite sensor electrodes that reduces or eliminates electrode deformation and resultant changes in sensor signaling.

BACKGROUND OF THE INVENTION

Sensors used to measure the presence of a particular substance in a liquid typically use metallic electrodes. Over a period of sensor use, these electrodes must be periodically cleaned. Today, cleaning of sensor electrodes is accomplished using a rotating ceramic cleaning and grinding "stone". The electrode to be cleaned is a relatively thin metallic ring set in a plastic base. To clean the electrode, a planar surface of the rotating ceramic stone is brought into contact with an exposed electrode ring surface that extends beyond the surface of the plastic base. As such, the rotation of the ceramic stone removes residue from the exposed surface of the electrode ring. Over time, both the electrode ring wears down and the ceramic stone wears down. When the ceramic stone wears down, a groove is formed in the formerly planar surface thereof. Upon using such a worn ceramic stone to clean an electrode, the groove formed in the surface of the ceramic stone modifies the grinding and cleaning capabilities of the ceramic stone. As a result, effective grinding and cleaning of the electrode is compromised. In cleaning and grinding an electrode with a worn ceramic stone, the electrode becomes "smeared out" or deformed over a portion of the surface of the adjacent plastic base in which the electrode is set. This smearing or deformation of the electrode changes the surface area and functioning of the electrode. As such, electrode deformation compromises the electrode's signaling capabilities. Because compromises to electrode signaling are unacceptable as causing detection inaccuracies, electrodes and ceramic stones for cleaning and grinding must be replaced often.

Due to capital costs and operational costs associated with frequent electrode and ceramic stone replacement, a need exists for improvement.

SUMMARY OF THE INVENTION

It is an object of the present invention to reduce groove-forming ceramic stone wear and electrode deformation over that of the prior art. The electrode sensor and ceramic stone apparatus and method of the present invention achieve this objective as well as others, as described below.

The present sensor useful for measuring the presence of a particular substance in a liquid includes an electrode manufactured from a metal, such as for example platinum, silver, gold or another metal of like characteristics. The metal electrode is fixed in a planar surface of a plastic base so as to be raised above the planar surface and amply exposed. In manufacturing the sensor, a plastic base is preferred due to cost considerations. However, other materials could likewise be used as a base for fixing the electrode, such as ceramic or glass. The base in which the metal electrode is set is preferably of like dimension and design as that of the prior art so as to be readily interchangeable therewith on existing equipment without requiring associated equipment modification(s).

The electrode fixed in the base is of an oval, elliptical, square or other non-circular shape, or non-symmetrically fixed circular shape. Sensors having electrodes of oval, elliptical, square or other non-circular shape, or non-symmetrically fixed circular shape, allows for improved electrode wear and a prolonged sensor operational life over that of the prior art sensor.

As noted briefly above, the present sensor is useful to detect and quantify an amount of a substance in a liquid, such as for example an amount of ions in a liquid or slurry or an amount of sulfite in water. However, with use, residue builds on the surface of the sensor electrode. With residue build-up, the electrode requires cleaning for residue removal therefrom to ensure proper and accurate sensor operation and function. Hence, periodically to remove residue from the electrode, the electrode is contacted with a relatively flat or planar contact surface of a rotating ceramic stone. The rotating ceramic stone is commonly referred to as a grinding and cleaning stone. Contact with the ceramic stone abrades the residue so as to again expose a clean electrode surface. Because the present electrodes are non-circular in shape, or if circular, non-symmetrically fixed, the planar surface of the ceramic stone contacting the electrodes is worn more evenly so as to reduce or eliminate groove formation therein. By reducing or eliminating groove formation in the relatively planar contact surface of the ceramic stone, deformation or "smearing" of the metal electrode cleaned thereby is likewise reduced or eliminated. As such, the useful operating life of both the sensor and the ceramic stone are significantly extended. Extending the useful operating life of both the sensor and the ceramic stone reduces both capital and operational costs associated therewith.

The present sensor for detection and measurement of a particular substance present in a liquid, comprises a base with an interior edge, an exterior edge and a top surface extending between the interior edge and the exterior edge, with a non-circular or non-symmetrical electrode fixed on said top surface for detection and measurement of a particular substance present in a liquid in which said sensor is submersed. The sensor base is manufactured from a plastic, glass or ceramic material. The sensor electrode is manufactured from a metal, such as from silver, gold, platinum or a combination thereof. The electrode is of a non-circular shape, such as oval, elliptical, square or an oscillating form. Alternatively, an electrode of circular shape may be used if non-symmetrically fixed to the sensor base. An example of a particular substance detected and measured by the sensor is sulfite present in water or ions present in a liquid or slurry.

A method of using the present sensor for detection and measurement of a particular substance present in a liquid, comprises submerging the sensor comprising a base with an interior edge, an exterior edge, a top surface extending between the interior edge and the exterior edge, and a non-circular or non-symmetrically fixed electrode on said top surface, in a liquid for detection and measurement of a particular substance present in the liquid and periodically cleaning residue from the electrode using a rotating ceramic stone. According to this method the sensor base is manufactured from a plastic, glass or ceramic material. The electrode is manufactured from a metal, such as silver, gold, platinum or a combination thereof. The non-circular electrode is oval, elliptical, square or an oscillating form. Alternatively, an electrode of circular shape may be used if non-symmetrically fixed to the sensor base. An example of a particular substance detected and measured by the sensor is sulfite present in water or ions present in a liquid or slurry.

A method of cleaning and grinding the present sensor electrode, comprises attaching a ceramic stone offset from center to a rotating arm so as to cause the ceramic stone to follow a non-circular path around the rotating arm, and contacting a sensor electrode with a contact surface of the ceramic stone for cleaning and grinding of residue from the sensor electrode with reduced wear or prevention of grooved wear of the contact surface.

Further objects and features of the present invention will be apparent from the following description and claims.

BRIEF DESCRIPTION OF THE DRAWINGS

The present invention is now described in more detail with reference to the appended drawings.

DETAILED DESCRIPTION OF THE INVENTION

Figure 1:
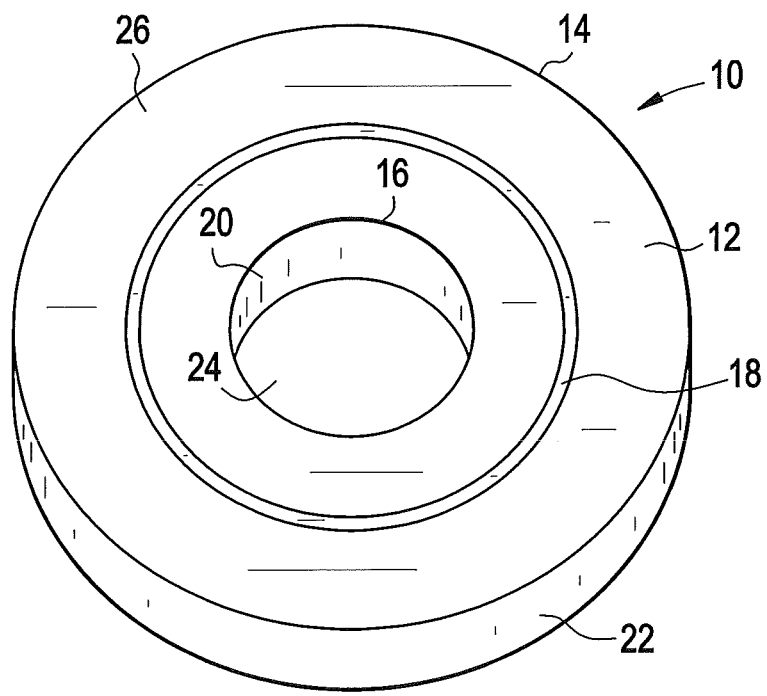
FIG. 1 is a top perspective view of an electrode sensor of the prior art.

Referring to FIG. 1, is a prior art sensor 10. Sensor 10 comprises a plastic base 12 defined by an exterior side surface 22 and an interior side surface 20. Interior side surface 20 defines a center aperture 24 through base 12. Extending between exterior side surface 22 and interior side surface 20 of base 12 is top surface 26 and opposed bottom surface (not shown). An interior edge 16 defines the intersection of top surface 26 and interior side surface 20. Likewise, an exterior edge 14 defines the intersection of top surface 26 and exterior side surface 22. Fixed in top surface 26 is a circular electrode 18 arranged symmetrically an equidistance between interior edge 16 and exterior edge 14. In use, electrode 18 is submerged in a liquid to detect and quantify a particular substance present in the liquid. Over time with such use, residue builds on electrode 18 requiring electrode 18 to be cleaned for continued proper operation and use.

Figure 2:
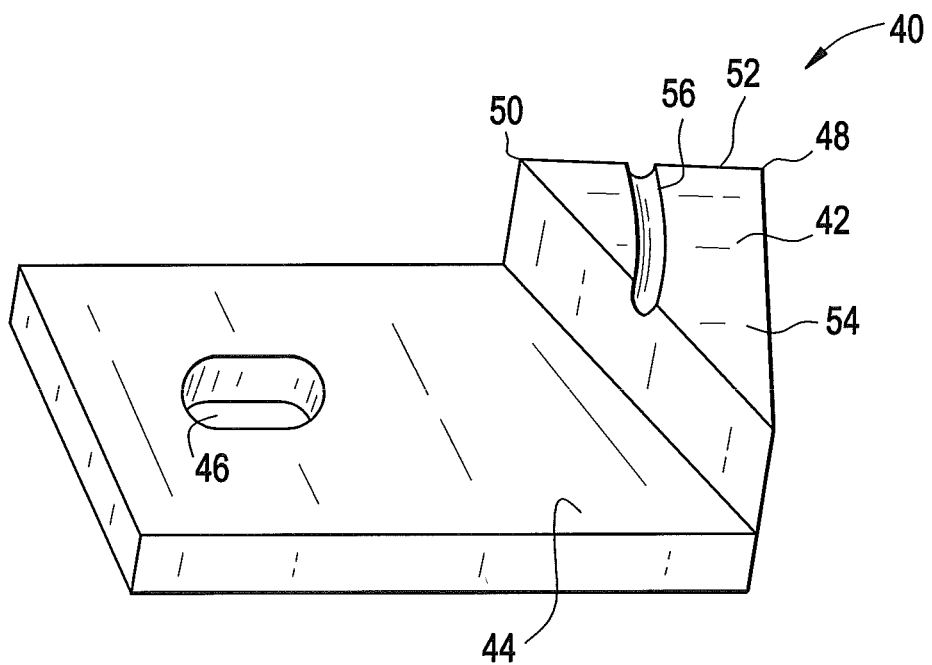
FIG. 2 is a top perspective view of the bottom of a worn rotating ceramic stone of the prior art.

Referring to FIG. 2, is a prior art ceramic stone 40 useful for cleaning and grinding electrodes 18 such as that of sensor 10. Ceramic stone 40 has a base 44 with an aperture 46 therethrough for removable attachment to a rotating arm (not shown) of associated equipment (not shown). Opposite aperture 46 on base 44 is an elevated contact member 42. Elevated contact member 42 includes a planar contact surface 54.

In using ceramic stone 40 to clean and grind electrode 18 of sensor 10, contact surface 54 is arranged for direct contact with electrode 18. As ceramic stone 40 rotates, leading side edge 52 of ceramic stone 40 moves over a portion of top surface 26 of sensor 10. As such, interior edge 50 of contact member 42 rotates over interior edge 16 of top surface 26. Likewise, exterior edge 48 of contact member 42 rotates over exterior edge 14 of top surface 26. Over time, as contact member 42 rotates over top surface 26 with contact surface 54 in direct contact with electrode 18, a groove 56 is worn into contact surface 54. Once contact surface 54 is worn to have a groove 56 therein, proper cleaning and grinding of electrode 18 is compromised.

Figure 3:
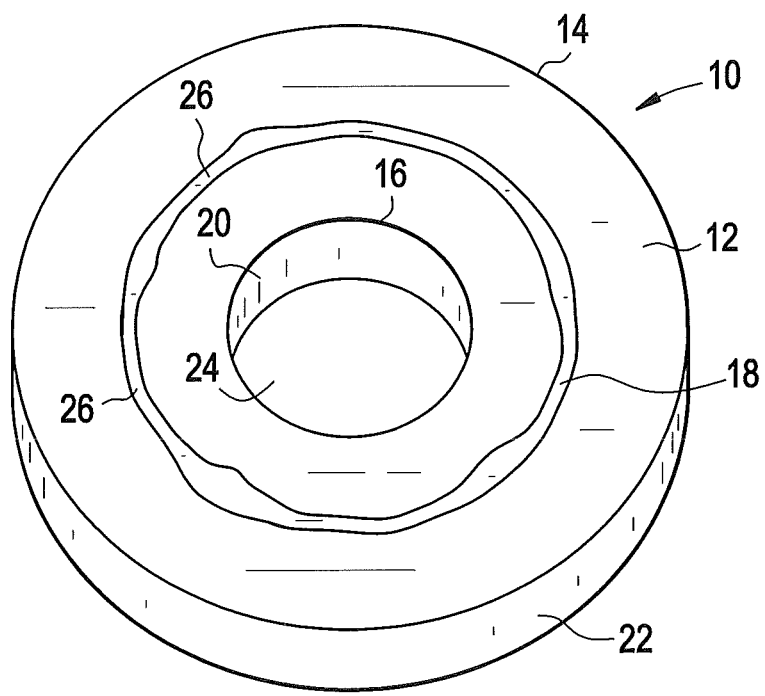
FIG. 3 is a top perspective view of the electrode sensor of FIG. 1 after having been contacted with the worn ceramic stone of FIG. 2.

As best illustrated in FIG. 3, is a sensor 10 deformed from cleaning and grinding with a ceramic stone 40 worn to have a groove 56 in contact surface 54. In rotation of ceramic stone 40 with groove 56 in direct contact with electrode 18 for cleaning and grinding of electrode 18 for removal of residue, electrode 18 is deformed by groove 56. Electrode 18 in its deformed state is "smeared out" over portions of base 12. As such, the surface area of electrode 18 is altered and proper operation and function of electrode 18 is compromised.

Figure 4:
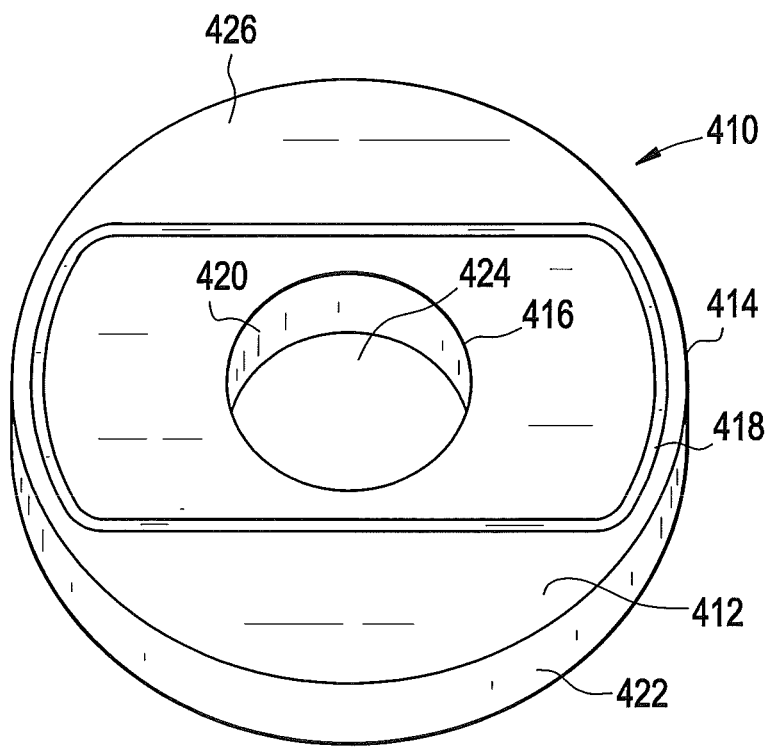
FIG. 4 is a top perspective view of a sensor according to the present disclosure.

To address the problem associated with wear to ceramic stone 40 and resultant deformation of electrode 18 as described above and illustrated in FIGS. 1 through 3, the present apparatus embodiment is disclosed herein and illustrated in FIG. 4. The present apparatus as illustrated in FIG. 4 has features in common with those illustrated in FIG. 1. As such, features illustrated in FIG. 4 common to those of FIG. 1 are signified using the same numbers but with the number "4" preceding them.

Illustrated in FIG. 4 is a sensor 410. Sensor 410 comprises a plastic base 412 defined by an exterior side surface 422 and an interior side surface 420. Interior side surface 420 defines a center aperture 424 through base 412. Extending between exterior side surface 422 and interior side surface 420 of base 412 is top surface 426 and opposed bottom surface (not shown). An interior edge 416 defines the intersection of top surface 426 and interior side surface 420. Likewise, an exterior edge 414 defines the intersection of top surface 426 and exterior side surface 422. Fixed in top surface 426 is a non-circular electrode 418 arranged with a varying distance between interior edge 416 and exterior edge 414. In use, electrode 418 is submerged in a liquid to detect and quantify a particular substance present in the liquid. Over time with such use, residue builds on electrode 418 requiring electrode 418 to be cleaned for continued proper operation and use.

In using a ceramic stone 40 in a method to clean and grind electrode 418 of sensor 410, contact surface 54 is arranged for direct contact with electrode 418. As ceramic stone 40 rotates, leading side edge 52 of ceramic stone 40 moves over a portion of top surface 426 of sensor 410. As such, interior edge 50 of contact member 42 rotates over interior edge 416 of top surface 426. Likewise, exterior edge 48 of contact member 42 rotates over exterior edge 414 of top surface 426. As contact member 42 rotates over top surface 426 with contact surface 54 in direct contact with electrode 418, no groove 56 is worn into contact surface 54 since non-circular electrode 418 is arranged with a varying distance between interior edge 416 and exterior edge 414. This variation in distance between interior edge 416 and exterior edge 414 reduces or prevents electrode 418 from wearing a groove 56 in contact surface 54 of ceramic stone 40. Hence, proper cleaning and grinding of electrode 418 is preserved, and the useful life of ceramic stone 40 is preserved, to achieve a prolonged operating life.

Figure 5:
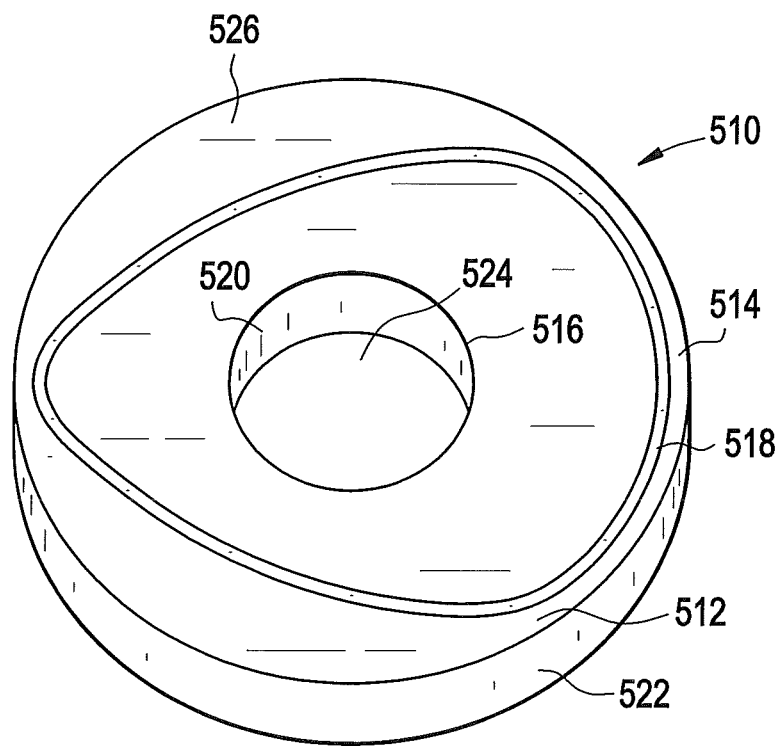
FIG. 5 is a top perspective view of another embodiment of a sensor according to the present disclosure.

Another embodiment to address the problems associated with wear to ceramic stone 40 and resultant deformation of electrode 18 as described above with reference to FIGS. 1 through 3, is disclosed herein and illustrated in FIG. 5. The present apparatus as illustrated in FIG. 5 has features in common with those illustrated in FIG. 1. As such, features illustrated in FIG. 5 common to those of FIG. 1 are signified using the same numbers but with the number "5" preceding them.

Illustrated in FIG. 5 is a sensor 510. Sensor 510 comprises a plastic base 512 defined by an exterior side surface 522 and an interior side surface 520. Interior side surface 520 defines a center aperture 524 through base 512. Extending between exterior side surface 522 and interior side surface 520 of base 512 is top surface 526 and opposed bottom surface (not shown). An interior edge 516 defines the intersection of top surface 526 and interior side surface 520. Likewise, an exterior edge 514 defines the intersection of top surface 526 and exterior side surface 522. Fixed in top surface 526 is a non-circular electrode 518 arranged with a varying distance between interior edge 516 and exterior edge 514. In use, electrode 518 is submerged in a liquid to detect and quantify a particular substance present in the liquid. Over time with such use, residue builds on electrode 518 requiring electrode 518 to be cleaned for continued proper operation and use.

In using a ceramic stone 40 in a method to clean and grind electrode 518 of sensor 510, contact surface 54 is arranged for direct contact with electrode 518. As ceramic stone 40 rotates, leading side edge 52 of ceramic stone 40 moves over a portion of top surface 526 of sensor 510. As such, interior edge 50 of contact member 42 rotates over interior edge 516 of top surface 526. Likewise, exterior edge 48 of contact member 42 rotates over exterior edge 514 of top surface 526. As contact member 42 rotates over top surface 526 with contact surface 54 in direct contact with electrode 518, no groove 56 is worn into contact surface 54 since non-circular electrode 518 is arranged with a varying distance between interior edge 516 and exterior edge 514. This variation in distance between interior edge 516 and exterior edge 514 reduces or prevents electrode 518 from wearing a groove 56 in contact surface 54 of ceramic stone 40. Hence, proper cleaning and grinding of electrode 518 is preserved, and the useful life of ceramic stone 40 is preserved, to achieve a prolonged operating life.

Figure 6:
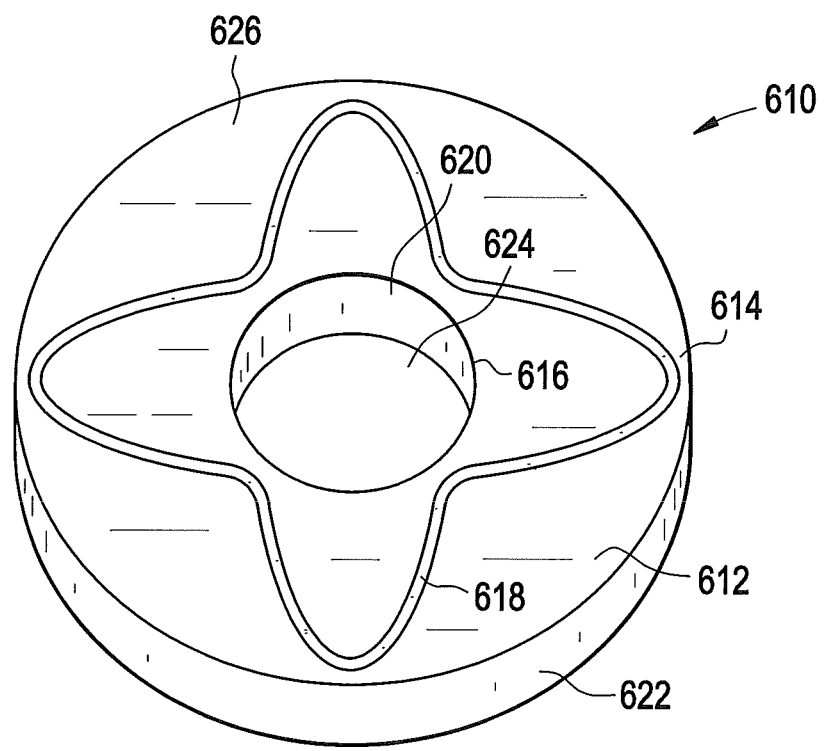
FIG. 6 is a top perspective view of another embodiment of a sensor according to the present disclosure.

Still another embodiment to address the problems associated with wear to ceramic stone 40 and resultant deformation of electrode 18 as described above with reference to FIGS. 1 through 3, is disclosed herein and illustrated in FIG. 6. The present apparatus as illustrated in FIG. 6 has features in common with those illustrated in FIG. 1. As such, features illustrated in FIG. 6 common to those of FIG. 1 are signified using the same numbers but with the number "6" preceding them.

Illustrated in FIG. 6 is a sensor 610. Sensor 610 comprises a plastic base 612 defined by an exterior side surface 622 and an interior side surface 620. Interior side surface 620 defines a center aperture 624 through base 612. Extending between exterior side surface 622 and interior side surface 620 of base 612 is top surface 626 and opposed bottom surface (not shown). An interior edge 616 defines the intersection of top surface 626 and interior side surface 620. Likewise, an exterior edge 614 defines the intersection of top surface 626 and exterior side surface 622. Fixed in top surface 626 is a non-circular electrode 618 arranged with a varying distance between interior edge 616 and exterior edge 614. In use, electrode 618 is submerged in a liquid to detect and quantify a particular substance present in the liquid. Over time with such use, residue builds on electrode 618 requiring electrode 618 to be cleaned for continued proper operation and use.

In using a ceramic stone 40 in a method to clean and grind electrode 618 of sensor 610, contact surface 54 is arranged for direct contact with electrode 618. As ceramic stone 40 rotates, leading side edge 52 of ceramic stone 40 moves over a portion of top surface 626 of sensor 610. As such, interior edge 50 of contact member 42 rotates over interior edge 616 of top surface 626. Likewise, exterior edge 48 of contact member 42 rotates over exterior edge 614 of top surface 626. As contact member 42 rotates over top surface 626 with contact surface 54 in direct contact with electrode 618, no groove 56 is worn into contact surface 54 since non-circular electrode 618 is arranged with a varying distance between interior edge 616 and exterior edge 614. This variation in distance between interior edge 616 and exterior edge 614 reduces or prevents electrode 618 from wearing a groove 56 in contact surface 54 of ceramic stone 40. Hence, proper cleaning and grinding of electrode 618 is preserved, and the useful life of ceramic stone 40 is preserved, to achieve a prolonged operating life.

Non-circular electrode 418, 518, 618 may be of any shape that varies the arranged distance of electrode 418, 518, 618 between interior edge 416, 516, 616 and exterior edge 414, 514, 614. Such shapes include oval, elliptical, square and oscillating forms. Less complex shapes and forms are preferred for ease in manufacture and thereby reduced cost. Alternatively, an electrode of circular shape may be used if non-symmetrically fixed to the sensor base. As such, the non-symmetrically fixed circular electrode would not be fixed to have a consistent equidistance between interior edge 16 and exterior edge 14.

Another approach to address the problems associated with wear to ceramic stone 40 and resultant deformation of electrode 18 as described above with reference to FIGS. 1 through 3, is to modify the attachment of the ceramic stone 40 through aperture 46 to a rotating arm (not shown) of associated equipment (not shown). As such, ceramic stone 40 is attached to the rotating arm (not shown) offset from center for offset revolution thereabout. With ceramic stone 40 no longer rotating along a circular path, but rather rotating along an oval path due to the offset revolution, groove 56 is not formed. For further explanation, by rotating ceramic stone 40 along an oval path, contact between electrode 18 and contact surface 54 is not static, but rather oscillates over a broader surface area of contact surface 54. Contact over a broader surface area of contact surface 54, reduces or prevents wearing of groove 56 in contact surface 54.

While the preferred embodiments has been shown and described in relation to apparatus and methods of cleaning and grinding sensor electrodes, various modifications may be made thereto by those skilled in the art without departing from the spirit and scope of the invention. Accordingly, it is to be understood that the invention has been described by way of illustration and is to be limited only in accordance with the claims appended hereto.

The invention claimed is:

1. A sensor for detection and measurement of a particular substance present in a liquid, comprising:
   a base with an interior edge, an exterior edge and a top surface extending between the interior edge and the exterior edge;
   a continuous non-circular or non-symmetrical electrode for varied distance of the continuous non-circular or non-symmetrical electrode from the interior edge and the exterior edge fixed on said top surface for detection and measurement of a particular substance present in a liquid in which said sensor is submersed, and a rotating ceramic stone to periodically clean residue from the continuous non-circular or non-symmetrical electrode without formation of an electrode dual side-abutting groove in the rotating ceramic stone, wherein the electrode dual side-abutting groove simultaneously abuts each side of the continuous non-circular or non-symmetrical electrode, due to the continuous non-circular or non-symmetrical electrode's varied distance from the interior edge and the exterior edge.

2. The sensor according to claim 1 wherein said base is manufactured from plastic, glass or ceramic material.

3. The sensor according to claim 1 wherein said electrode is manufactured from a metal.

4. The sensor according to claim 1 wherein said electrode is manufactured from silver, gold, platinum or a combination thereof.

5. The sensor according to claim 1 wherein said particular substance is sulfite.

6. The sensor according to claim 1 wherein said liquid is water.

7. A method of using a sensor for detection and measurement of a particular substance present in a liquid, comprising:

submerging a sensor comprising a base with an interior edge, an exterior edge, a top surface extending between the interior edge and the exterior edge, and a continuous non-circular or non-symmetrical electrode for varied distance of the continuous non-circular or non-symmetrical electrode from the interior edge and the exterior edge fixed on said top surface, in a liquid for detection and measurement of a particular substance present in said liquid; and periodically cleaning residue from the continuous non-circular or non-symmetrical electrode using a rotating ceramic stone without formation of an electrode dual side-abutting groove in the rotating ceramic stone, wherein the electrode dual side-abutting groove simultaneously abuts each side of the continuous non-circular or non-symmetrical electrode, due to the continuous non-circular or non-symmetrical electrode's varied distance from the interior edge and the exterior edge.

8. The method according to claim 7 wherein said base is manufactured from plastic, glass or ceramic material.

9. The method according to claim 7 wherein said electrode is manufactured from a metal.

10. The method according to claim 7 wherein said electrode is manufactured from silver, gold, platinum or a combination thereof.

11. The method according to claim 7 wherein said particular substance is sulfite.

12. The method according to claim 7 wherein said liquid is water.

* * * * *